United States Patent [19]
Yamada

[11] Patent Number: 5,811,666
[45] Date of Patent: Sep. 22, 1998

[54] APPARATUS AND METHOD FOR CHROMATOGRAPHIC ANALYSIS USING PRESSURE CHANGES TO IDENTIFY THE SAMPLE

[75] Inventor: Yoshiaki Yamada, Ishioka, Japan

[73] Assignee: Hitachi, Ltd., Tokyo, Japan

[21] Appl. No.: 728,374

[22] Filed: Oct. 9, 1996

[30] Foreign Application Priority Data

Oct. 13, 1995 [JP] Japan ................................ 7-265356

[51] Int. Cl.⁶ .................................................... B01D 15/08
[52] U.S. Cl. .......................................... 73/61.56; 73/61.52
[58] Field of Search ................................ 73/19.05, 23.35, 73/23.36, 23.37, 23.38, 23.4, 23.41, 23.42

[56] References Cited

U.S. PATENT DOCUMENTS

| | | | |
|---|---|---|---|
| 4,117,727 | 10/1978 | Friswell et al. | 73/422 |
| 4,414,839 | 11/1983 | Dilley et al. | 73/23 |
| 5,610,835 | 3/1997 | Dominguez et al. | 364/497 |

FOREIGN PATENT DOCUMENTS

| | | |
|---|---|---|
| 60-11690 | 1/1985 | Japan . |
| 60-161558 | 8/1985 | Japan . |
| 62-194465 | 8/1987 | Japan . |
| 1-142461 | 6/1989 | Japan . |
| 4-184167 | 7/1992 | Japan . |
| 6-19361 | 3/1994 | Japan . |
| 6-19362 | 3/1994 | Japan . |

*Primary Examiner*—Scott W. Houtteman
*Attorney, Agent, or Firm*—Fay, Sharpe, Beall, Fagan, Minnich & McKee

[57] ABSTRACT

A method for chromatographic analysis wherein an eluent is fed by a pump and a sample is injected into the eluent from a sample injector, while the composition of the eluent is changed over time. A mixture of the eluent and the sample is passed through a column, and identification of the sample is performed based on separation of the sample into components in the column. The pressure of the eluent in a feed path is detected, a pressure depending on the composition of the eluent is obtained as a reference and the detected pressure is compared with the obtained pressure. Such a comparison enables abnormality in an apparatus for liquid chromatographic analysis to be easily detected. The apparatus for carrying out the chromatographic analysis includes a pressure sensor for detecting the pressure of the eluent in a feed path, a pressure memory for storing the pressure values detected at certain time intervals from the start of measurement as a data file of pressure transition data for each sample, a selector for, when an unknown sample is measured, selecting the pressure transition data, which is to be compared as a reference, from data files store beforehand, and a comparator for comparing the pressure values of the unknown sample detected by the pressure sensor and the values of the pressure transition data selected by the selector and determining an agreement between both the values.

10 Claims, 9 Drawing Sheets

FIG. 4

COMPARISON OF PRESSURE TRANSITION FILES

◉ MAKE COMPARISON   ○ MAKE NO COMPARISON

PRESSURE TRANSITION FILE TO BE COMPARED

○ FILE RESULTED FROM ANALYZING
  STANDARD SAMPLE (STD)

◉ DESIGNATE BY FILE NAME
  PAH001

THRESHOLD VALUE OF PRESSURE TRANSITION AGREEMENT 0.9 – 1.1

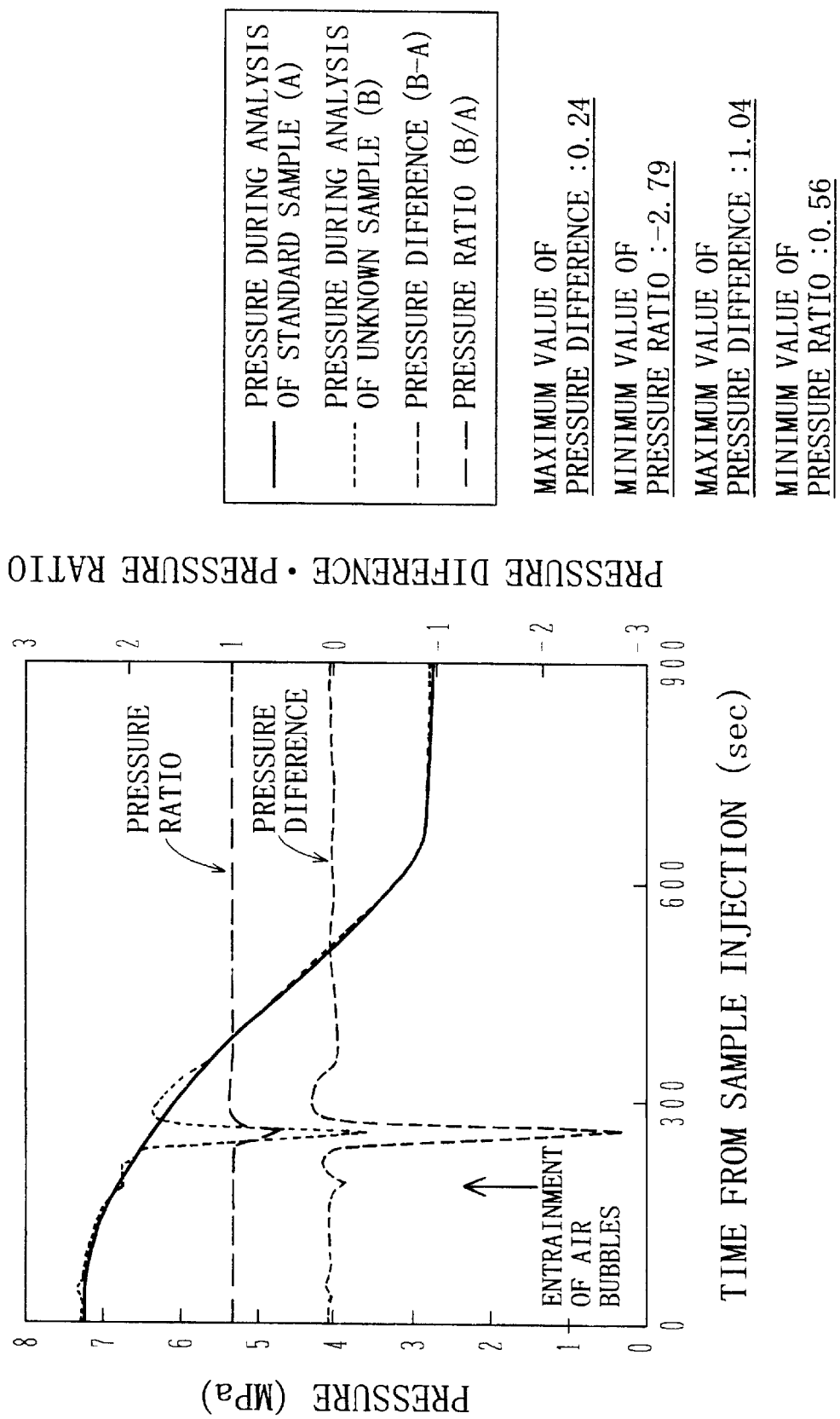

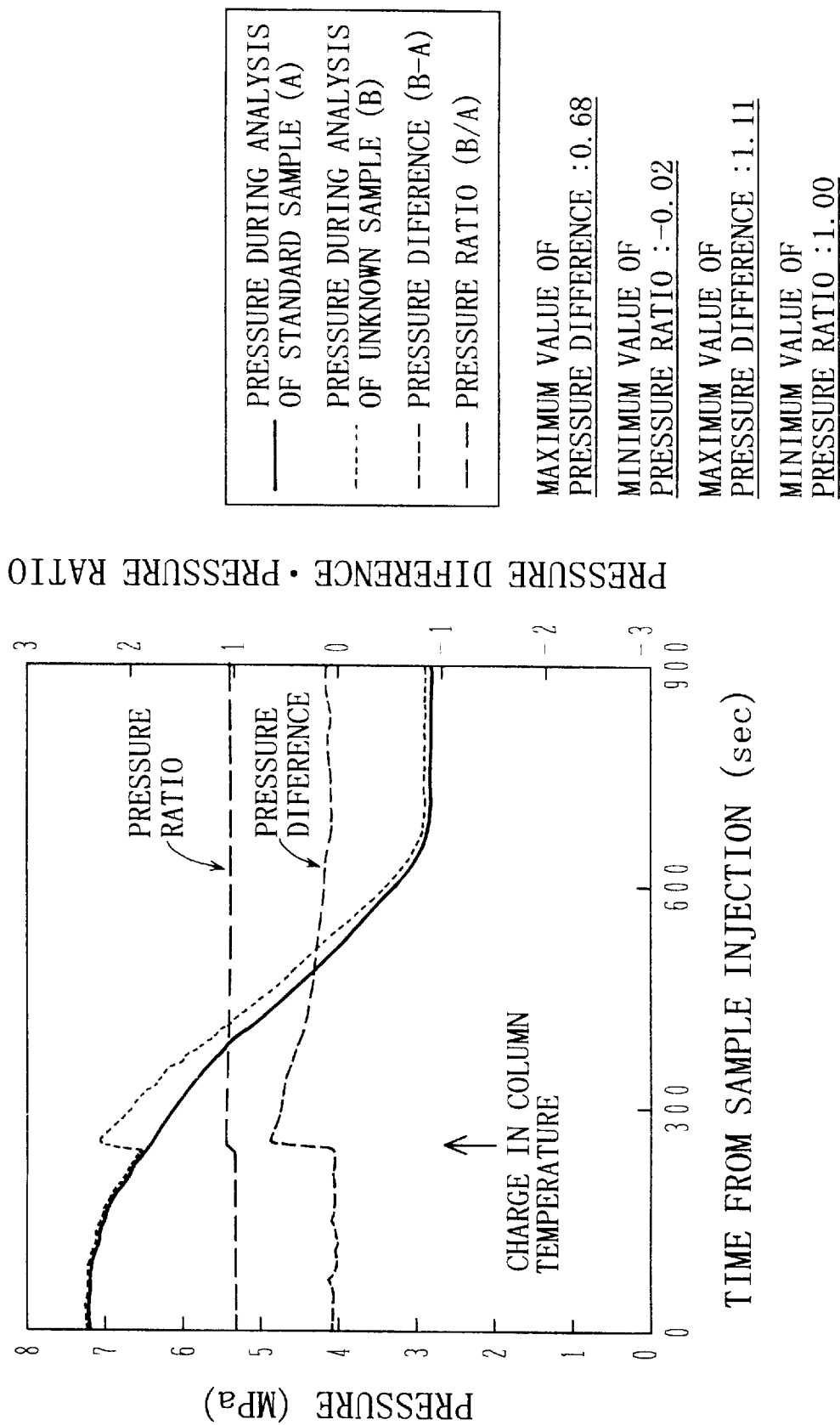

FIG. 8

ANALYSIS RESULT REPORT

ANALYSIS DATE : 08/31/94 10:20
OUTPUT DATE   : 09/01/94 10:40

ANALYTICAL PROCESS FILE : AROMATIC HYDROCARBON(PAH. MTH)
DATA FILE     : PAH006. RW1
PRESSURE FILE : PAH006. PRS

| PEAK No. | RETENTION TIME (min) | COMPORNENT NAME | AREA (μV·s) | CONCENTRATION (ppm) |
|---|---|---|---|---|
| 3 | 2.02 | BENZENE | 300528 | 0.200 |
| 4 | 2.44 | NAPHTHALENE | 66132 | 3.200 |
| 5 | 2.60 | DIPHENYL | 532309 | 3.400 |
| 6 | 3.24 | PHENANCENE | 1267168 | 3.300 |
| 7 | 3.91 | FLUORACENE | 329696 | 3.300 |
| 8 | 4.44 | PYRENE | 305925 | 3.700 |
| 9 | 5.18 | CHRYSENE | 678687 | 3.100 |
| 12 | 8.37 | BENZPYRENE | 747336 | 4.200 |

PRESSURE TRANSITION AGREEMENT : 1.02
PRESSURE FILE TO BE COMPARED  : PAH001. PRS

FIG. 9

ANALYSIS RESULT REPORT

ANALYSIS DATE : 08/31/94 10:20
OUTPUT DATE   : 09/01/94 10:40

ANALYTICAL PROCESS FILE : AROMATIC HYDROCARBON(PAH.MTH)
DATA FILE     : PAH006.RW1
PRESSURE FILE : PAH006.PRS

| PEAK No. | RETENTION TIME (min) | COMPORNENT NAME | AREA ($\mu V \cdot s$) | CONCENTRATION (ppm) |
|---|---|---|---|---|
| 3  | 2.02 | BENZENE     | 300528 | 0.200 |
| 4  | 2.44 | NAPHTHALENE | 66132  | 3.200 |
| 5  | 2.60 | DIPHENYL    | 532309 | 3.400 |
| 8  | 4.44 | PYRENE      | 127468 | 1.542 |
| 9  | 5.18 | CHRYSENE    | 399343 | 1.652 |
| 12 | 8.37 | BENZPYRENE  | 971537 | 5.460 |

PRESSURE TRANSITION AGREEMENT : 0.56 (PRESSURE TRANSITION IS ABNORMAL)
PRESSURE FILE TO BE COMPARED : PAH001.PRS

APPARATUS AND METHOD FOR CHROMATOGRAPHIC ANALYSIS USING PRESSURE CHANGES TO IDENTIFY THE SAMPLE

BACKGROUND OF THE INVENTION

1. Field of the Invention

The present invention relates to an apparatus and a method for chromatographic analysis by which a sample is injected into an eluent fed by a pump, a mixture of the sample and the eluent is passed through a column, and the sample is identified based on separation into components which occurs in the column.

2. Description of the Related Art

An apparatus for chromatographic analysis includes the steps of feeding an eluent by a pump, injecting a sample into the eluent from a sample injector, passing a mixture of the sample and the eluent through a column, and performing identification and quantitative measurement of the sample by a data processor based on component peaks which occurs in the column. Information about the pressure of the eluent fed by the pump is very effective in determining whether the apparatus for chromatographic analysis is operating normally or not.

In one conventional apparatus for chromatographic analysis, the pressure of an eluent is detected when the eluent is injected, and the detected pressure value is recorded on recording paper. But such an apparatus for chromatographic analysis merely records the detected pressure value and is unable to determine from information data of the detected pressure as to whether the apparatus is normal or abnormal. There is also a known apparatus wherein the pressure after injection of a sample is continuously detected and an alarm message is displayed if a pressure change occurs. Also, there are known methods for determining abnormality in the operation of apparatus from a pressure transition in a like manner to the above prior art. JP-B-6-19361 discloses a method of determining abnormality of the apparatus based on a sudden change in the detected pressure, and JP-B-6-19362 discloses a method of determining abnormality of the apparatus based on an integrated value of the detected pressure.

In an apparatus for chromatographic analysis, when one objective sample is analyzed while changing the composition of an eluent, the eluent pressure varies during the analysis. However, the prior art methods disclosed in the above-cited JP-B-6-19361 and JP-B-6-19362 do not take into consideration a pressure change which occurs when the eluent composition is changed. These prior art methods, therefore, have had the problem that when the eluent composition is changed as per setting, the resulting pressure change is judged as a sudden change or abnormality of the pressure integrated value and then recognized as an abnormality of the apparatus.

Further, the prior art methods disclosed in the above-cited JP-B-6-19361 and JP-B-6-19362, which intend to determine abnormality of the apparatus based on a pressure transition, are very effective for the case where the same eluent is fed under the same conditions at all times during the analysis, but are not adaptable for the case where the conditions of feeding an eluent are different, depending on samples to be analyzed.

SUMMARY OF THE INVENTION

An object of the present invention is to provide an apparatus and a method for chromatographic analysis which can easily determine or not whether the apparatus has operated normally.

Another object of the present invention is to provide an apparatus and a method for chromatographic analysis which can easily and objectively determine whether or not the apparatus has operated normally, even when the composition and/or feeding conditions of an eluent are changed during the analysis.

To achieve the above objects, according to the present invention, a pressure depending on the composition of an eluent is obtained and compared with the actually detected pressure.

Preferably, according to the present invention, in an apparatus for chromatographic analysis including the steps of feeding an eluent by a pump, injecting a sample into the eluent from a sample injector, passing a mixture of the eluent and the sample through a column, and performing identification and quantitative measurement of the sample by a data processor based on component peaks which occur in the column, the apparatus comprises a pressure sensor for detecting the pressure of the eluent in a feed path, a pressure memory for storing the pressure values detected at certain time intervals from the start of measurement as a data file of pressure transition data for each sample, a selector for, when an unknown sample is measured, selecting the pressure transition data, which is to be compared as a reference, from data files stored beforehand, and a comparator for comparing the pressure values of the unknown sample detected by the pressure sensor and the values of the pressure transition data selected by the selector and determining any agreement or match between both the values as a result of the comparison of the values.

Thus, with the present invention, a pressure depending on the composition of an eluent is obtained for use as a reference and the actually detected pressure is compared with the obtained pressure. Therefore, even when the composition of the eluent is changed, the appropriate reference pressure can be estimated and proper judgment as to whether the apparatus is normal or not can be made by comparing the actually detected pressure with the estimated pressure.

Also preferably, the pressure of the eluent in the feed path is detected by the pressure sensor, and the pressure values detected at certain time intervals from the start of measurement are stored in the pressure memory as a data file of pressure transition data for each sample. The data file to be thus stored may be either pressure transition data of a standard sample (i.e., a sample for which components and concentrations are known beforehand) or pressure transition data of an objective sample which has been analyzed in the past. When an unknown sample (i.e., an objective sample to be analyzed for which components and concentrations are not yet known) is measured, the pressure transition data to be compared or used as a reference is selected by the selector from data files stored as mentioned above, and the comparator compares the pressure values of the unknown sample detected by the pressure sensor and the values of the pressure transition data selected by the selector and determines an agreement or match between both the values.

Here, if the composition and/or feeding conditions of the eluent are set to be the same between during measurement of a standard sample or an objective sample analyzed in the past and during measurement of an unknown sample, the pressure transition of the eluent should also be the same therebetween. Accordingly, by selecting an appropriate one of the pressure transition data which has resulted from analyzing a standard sample or an objective sample in the past under the same conditions through the selector, and comparing the selected pressure transition data with the pressure transition data resulted from detecting an unknown sample and determining an agreement or match between both the data in the comparator as a result of the comparison, whether the apparatus is operating normally or not can be easily and objectively judged. Further, since the pressure transition data resulted from detecting an unknown sample is compared with the pressure transition data resulted from analyzing a standard sample or an objective sample in the past under the same conditions, the present invention is of course adaptable for the case where analysis is performed while changing the composition and/or feeding conditions of the eluent.

In the above apparatus for chromatographic analysis, preferably, the comparator calculates, as a numeral value, the agreement or match between the detected pressure values of the unknown sample and the values of the pressure transition data selected from the data files in the same instant after the start of measurement. Also preferably, the comparator takes differences or ratios between the detected pressure values of the unknown sample and the values of the pressure transition data selected from the data files.

With such an arrangement, because the comparator indicates, as a numeral value, the agreement or match in pressure transition between the unknown sample and the reference as a result of the comparison, the agreement can be more easily and objectively judged. In this connection, by indicating the agreement as a numerical value by taking differences or ratios between the values, judging the agreement can be made very easy.

Preferably, the apparatus further comprises an output unit for outputting the agreement calculated as a numerical value by the comparator along with the results of the identification and the quantitative measurement of the sample.

With this arrangement, the agreement calculated as a numerical value by the comparator can be output from the output unit along with the results of the identification and the quantitative measurement of the sample.

Preferably, the apparatus further comprises a threshold value setting unit for presetting threshold values for the agreement calculated as a numerical value, the comparator compares the agreement calculated as a numerical value and the threshold values, and the output unit outputs an alarm message when the agreement calculated as a numerical value is not within the range of the threshold values.

By so presetting appropriate threshold values for the agreement calculated as a numerical value through the threshold value setting unit, comparing the agreement calculated as a numerical value and the threshold values in the comparator, and outputting an alarm message from the output unit when the agreement calculated as a numerical value is not within the range of the threshold values, whether the apparatus is operating normally or not can be more easily and objectively judged.

BRIEF DESCRIPTION OF THE DRAWINGS

FIG. 4 shows one example of a screen image displayed on a display portion when pressure transition data to be compared as a reference is selected from data files.

FIG. 6 is a chart which has resulted from comparing the pressure during analysis of the standard sample with pressure changed when air bubbles were entrained into a feed path of the eluent during analysis of the unknown sample, in a similar manner as FIG. 5.

FIG. 7 is a chart resulted from comparing the pressure during analysis of a standard sample with pressure changed when the column temperature was varied due to an abnormality of a column thermostat during analysis of the unknown sample, in a similar manner as FIG. 5.

FIG. 8 is a representation of one example of an analysis result report obtained by the apparatus for chromatographic analysis shown in FIG. 1, the representation indicating the case where the apparatus is normally operating.

FIG. 9 is a representation of another example of an analysis result reports obtained by the apparatus for chromatographic analysis shown in FIG. 1, the representation indicating the case where the apparatus has an abnormality in operation.

DETAILED DESCRIPTION OF THE PREFERRED EMBODIMENTS

One preferred embodiment of an apparatus for chromatographic analysis according to the present invention will be described below with reference to FIGS. 1 to 9.

Figure 1:
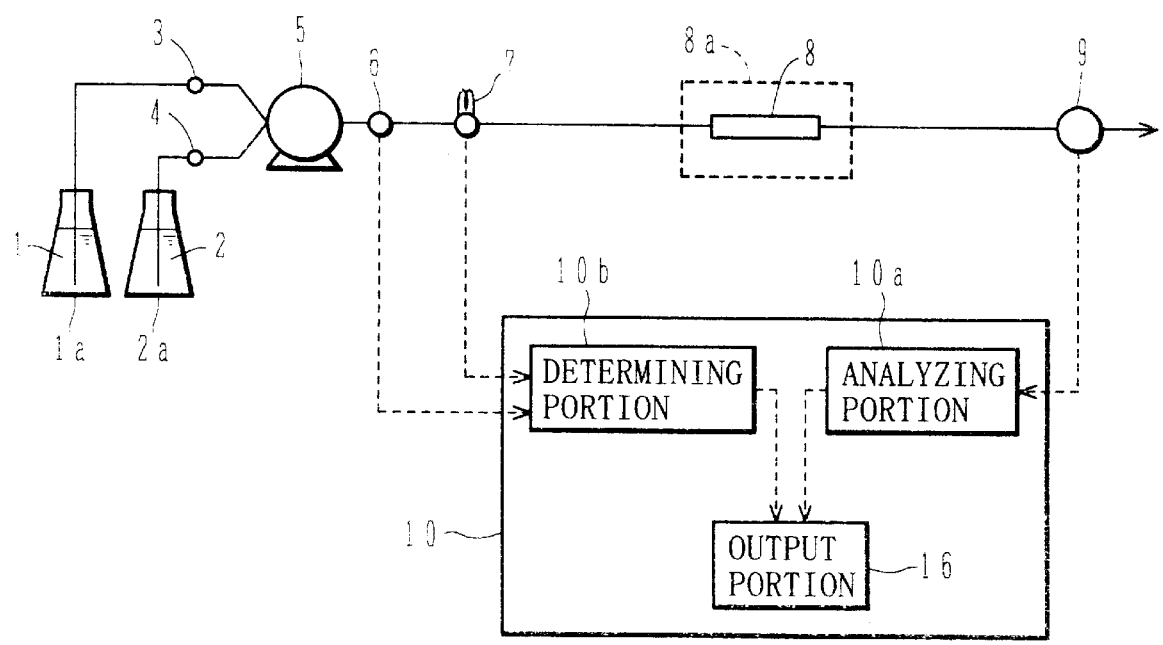
FIG. 1 is a block diagram of an apparatus for chromatographic analysis according to one embodiment of the present invention.

FIG. 1 is a block diagram of the apparatus for chromatographic analysis according to this embodiment. Eluents 1, 2 contained respectively in eluent bottles 1a, 2a are fed under pressure by a pump 5. Here, by opening and closing valves 3, 4, the composition of a mixture of the eluents 1, 2, i.e., the composition of an eluent to be fed, can be changed. A sample is injected from a sample injector 7 into a flow path of the eluent and, thereafter, the sample mixed into the eluent is separated into respective components in a column 8. The column 8 is installed in a column thermostat 8a to avoid temperature variation. A change in the effluent from the column 8 is converted by a detector 9 into an electric signal which is sent to an analyzing portion 10a of a data processor 10. The analyzing portion 10a performs identification of the components from the retention time of each component peak and quantitative measurement of the component from the area or height of each component peak. A pressure sensor 6 is disposed downstream of the pump 5 and a pressure value detected by the pressure sensor 6 is sent to a determining portion 10b of the data processor 10.

Figure 2:
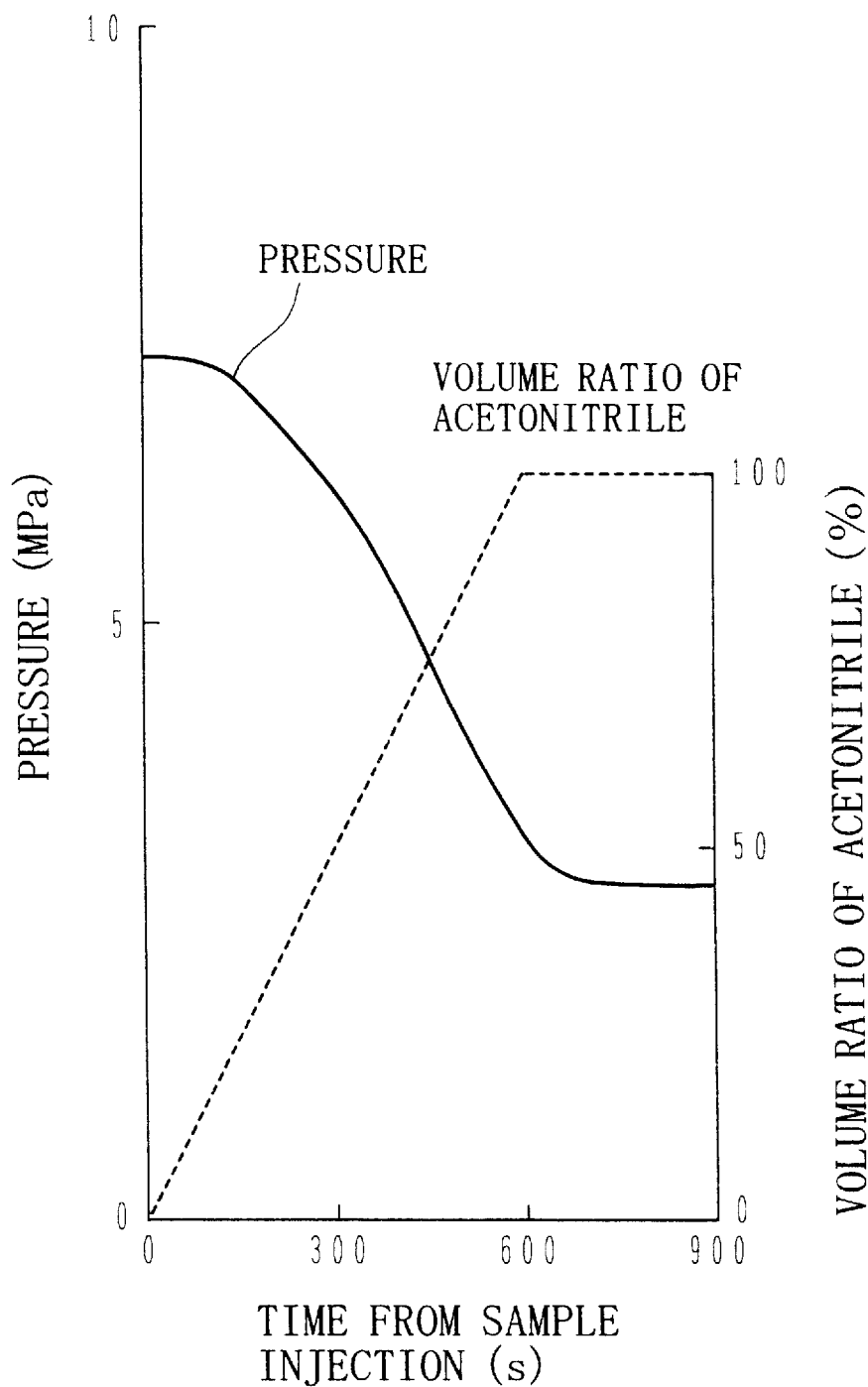
FIG. 2 is a chart showing an example of pressure change from injection of a sample which has resulted when analysis was performed while changing the composition of an eluent, the chart showing the case where a column was filled with silica into which an octadecile radical was introduced, and acetonitrile was employed as the eluent.

FIG. 2 is a chart showing an example of pressure change from injection of a sample which has resulted when analysis was performed while changing the composition of an eluent. In this example, the column 8 was filled with silica into which an octadecile radical was introduced, and acetonitrile was employed as the eluent. As shown in FIG. 2, an increase in the volume ratio of acetonitrile diminishes the column resistance and hence reduces the pressure when the eluent is passed through the column at a constant flow rate. The prior art methods disclosed in the above-cited JP-B-6-19361 and JP-B-6-19362 recognize such a pressure change caused by change in composition of the eluent as an abnormality of the apparatus and, therefore, cannot be applied to the analysis that is performed while changing the composition of the eluent. Further, as mentioned before, those prior art methods are very effective for the case where the same eluent is fed under the same conditions at all times during the analysis, but are not adaptable for the case where the conditions of feeding an eluent are made different depending on samples to be analyzed. By contrast, with this embodiment, whether the apparatus has operated normally or not can be judged from the arrangement described below, even when the composition and/or feeding conditions of the eluent are changed during the analysis.

Figure 3:
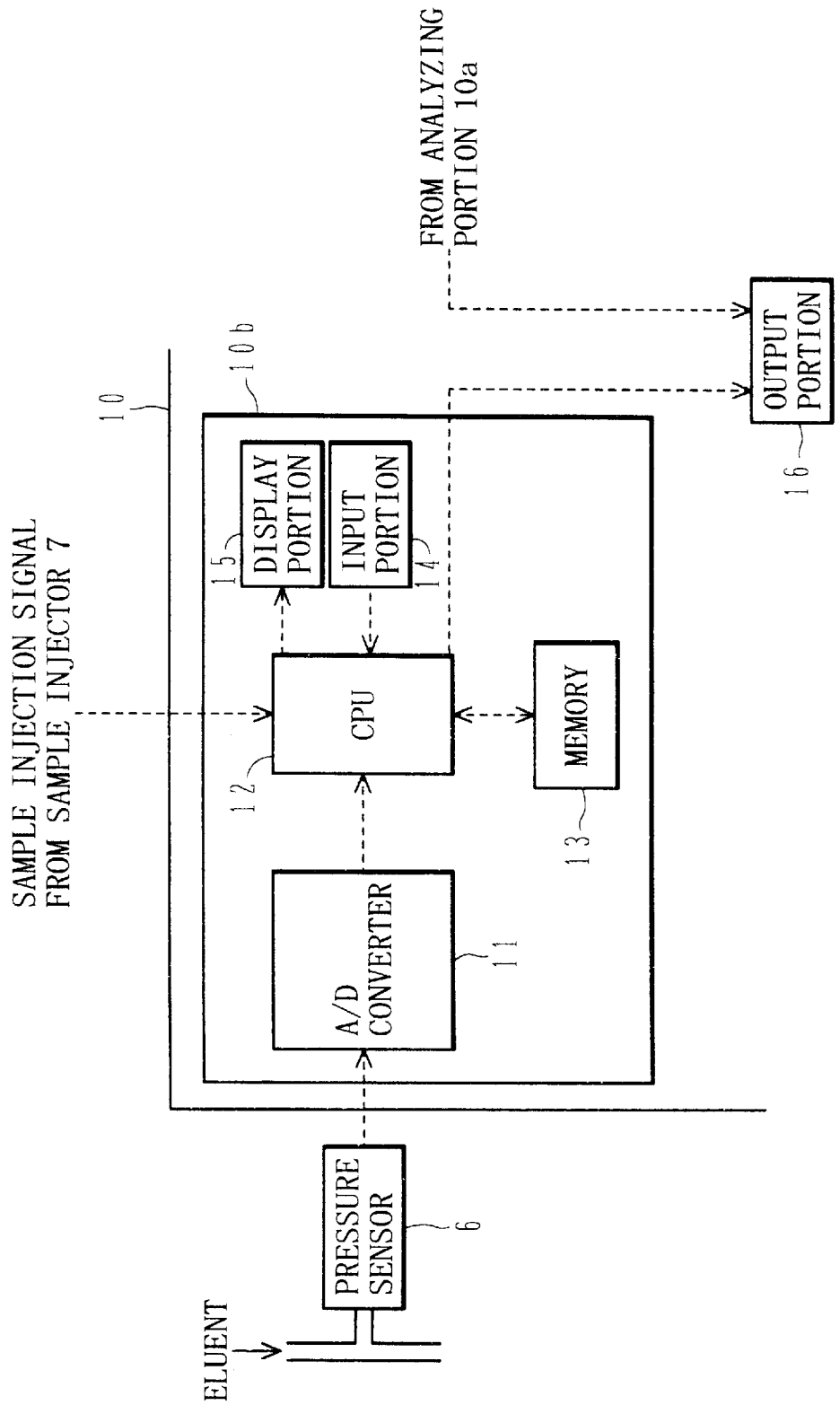
FIG. 3 is a diagram showing the configuration of a determining section of a data processor in FIG. 1.

FIG. 3 is a diagram showing the configuration of the determining portion 10b of the data processor 10 in the apparatus for chromatographic analysis of this embodiment. The pressure value of the eluent detected by the pressure sensor 6 is converted into an electric signal which is sent to an A/D converter 11 in the determining portion 10b and then sent to a CPU 12 in the digital form. Upon receiving a sample injection signal from the sample injector 7, the CPU 12 stores data of the detected pressure value in a memory 13 at constant time intervals previously determined. When a certain time elapses from the start of storing the pressure value data, or after completion of the analysis, a set of the pressure value data is named as pressure transition data and stored as a data file in the memory 13 again. The data file to be thus stored in the memory 13 is either pressure transition data of a standard sample (i.e., a sample for which components and concentrations are known beforehand) or pressure transition data of an objective sample which has been analyzed in the past.

Then, when an unknown sample (i.e., an objective sample to be analyzed for which components and concentrations are not yet known) is measured, the pressure transition data to be compared as a reference is selected from data files and a comparison is made in the CPU 12 between the pressure values of the unknown sample detected by the pressure sensor 6 and the values of the pressure transition data selected from the data files. An agreement or match between both the values is determined in terms of difference therebetween or ratio of one to the other. When selecting the pressure transition data to be compared as a reference from the data files, this selection is effected through an input portion 14 and the selected data is displayed on a display portion 15. Also, the detected pressure values of the unknown sample are stored in one data file to be utilized as the pressure transition data to be compared as a reference in subsequent analysis. The comparison result (pressure transition agreement) in the CPU 12 is output from an output portion 16 along with the results of identification and quantitative measurement of the components obtained in the analyzing portion 10a. Those results can be output from the output portion 16 by any of various ways such as being displayed on a TV screen, printed out on recording paper using a printer, and recorded on a floppy disk or the like.

FIG. 4 shows one example of a screen image displayed on the display portion 15 when pressure transition data to be compared as a reference with an unknown sample is selected from data files. When analyzing an unknown sample, it is usual to analyze a standard sample immediately before the objective analysis and then analyze the unknown sample under the same conditions. Therefore, the pressure transition data to be compared as a reference is preferably provided by the pressure transition data which has been obtained by analyzing the standard sample immediately before the objective analysis as mentioned above. Alternatively, the pressure transition data to be compared as a reference may be the pressure transition data obtained by analyzing another objective sample in the past, rather than being obtained from the immediately preceding analysis of the standard sample. FIG. 4 shows a screen image enabling the operator to selectively designate either the file which has resulted from analyzing the standard sample or the file which has resulted from analyzing the sample at earlier time by the file name. Also, threshold values of the pressure transition agreement are set so as to cover a certain range around 0 when the agreement is determined based on the difference, and a certain range around 1 when the agreement is determined based on the ratio. In FIG. 4, on an assumption that the agreement is determined based on the ratio, the threshold values are set so as to cover the range of 0.9 to 1.1.

Figure 5:
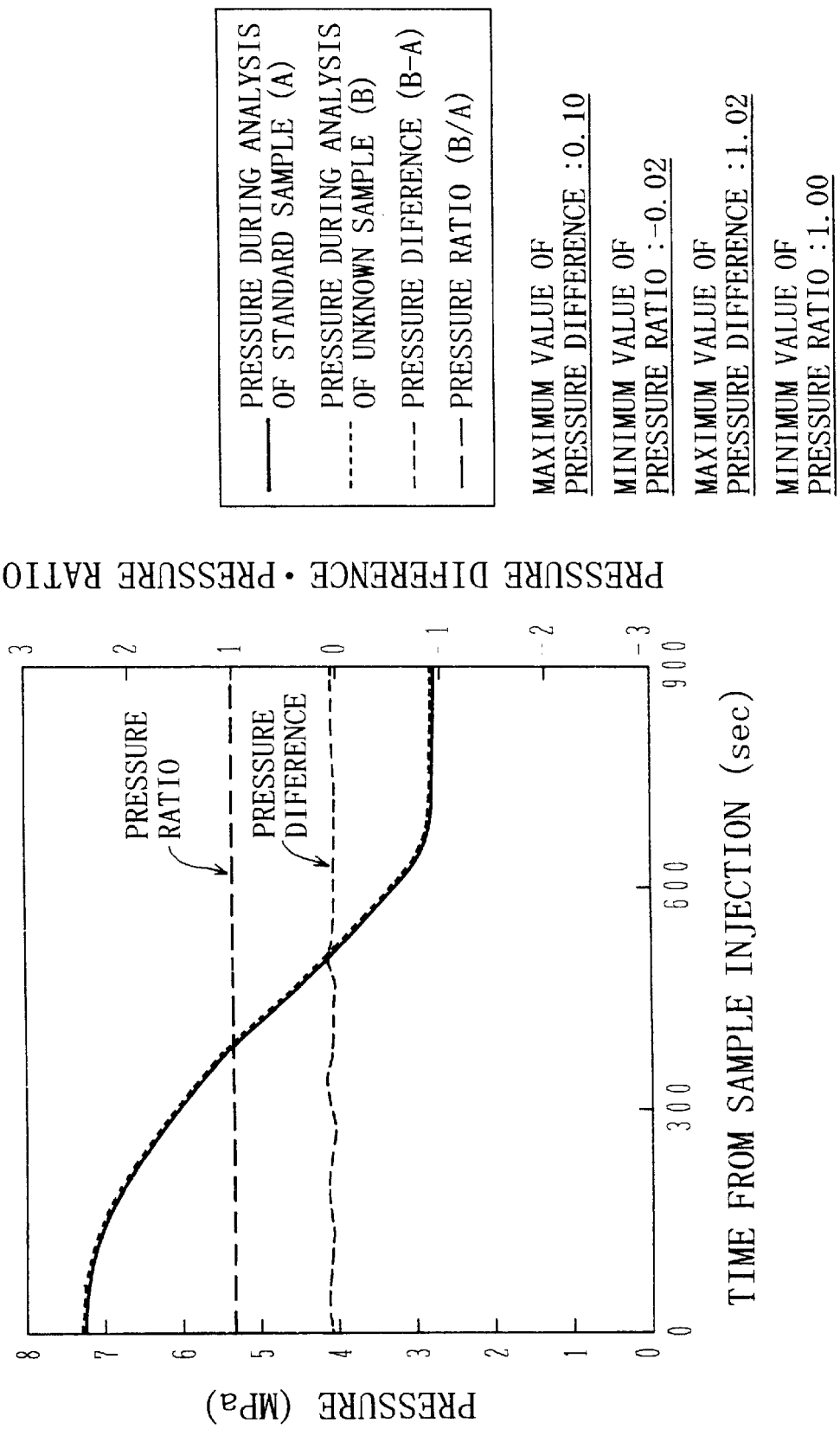
FIG. 5 is a chart which has resulted from detecting and storing pressures during analysis of a standard sample and an unknown sample at time intervals of 10 seconds from the sample injection, comparing the pressure values in the same instant after the sample injection to each other, and determining an agreement between both the pressure values.

FIG. 5 is a chart which has resulted from detecting and storing pressures during analysis of a standard sample under the same conditions as in FIG. 2 at time intervals of 10 seconds from the sample injection, detecting and storing pressures during analysis of an unknown sample under the same conditions in a like manner, and comparing the pressure values in the same instant after the sample injection, to each other. The agreement or match between both the pressure values is represented by the difference therebetween and the ratio of one to the other. When the apparatus has operated normally, the pressure transitions during the analysis are so very close between the standard sample and the unknown sample that, comparing the pressure value data in the same instant after the sample injection to each other, the difference therebetween falls in the range of—0.02 to 0.10 MPa and the ratio of one to the other falls in the range of 1.00 to 1.02.

FIG. 6 is a chart which has resulted from comparing the pressure during analysis of a standard sample with pressure changed when air bubbles were entrained into a feed path of the eluent (acetonitrile) during analysis of the unknown sample, in a similar manner as FIG. 5. With the entrainment of air bubbles into the feed path, the pressure during analysis of the unknown sample was lowered near 260 seconds after the sample injection in comparison with the pressure during analysis of the standard sample. Further, since the acetonitrile could not be fed (sucked) as per setting, the concentration of acetonitrile was reduced during analysis of the unknown sample down to a lower value than during analysis of the standard sample and a rise in pressure during analysis of the unknown sample appeared near 300 seconds after the sample injection. In this case, comparing the pressure value data in the same instant after the sample injection to each other, the difference therebetween ranges from −2.79 to 0.24 MPa and the ratio of one to the other ranges from 0.56 to 1.04. It is therefore understood that the ranges of the difference and the ratio are apparently significantly different from the ranges to be obtained when the apparatus has operated normally.

FIG. 7 is a chart which has resulted from comparing the pressure during analysis of a standard sample with pressure changed when the temperature of the column 8 was varied due to abnormality of the column thermostat 8a during analysis of the unknown sample, in a similar manner as FIG. 5. With a temperature drop of the column 8, the pressure during analysis of the unknown sample was raised after 250 seconds after the sample injection in comparison with the pressure during analysis of the standard sample. In this case, comparing the pressure value data in the same instant after the sample injection to each other, the difference therebetween ranges from—0.02 to 0.68 MPa and the ratio of one to the other ranges from 1.00 to 1.11. It is therefore understood that the ranges of the difference and the ratio are apparently significantly different from the ranges to be obtained when the apparatus has operated normally, as with the above case of air bubbles being entrained in FIG. 6.

Thus, by detecting and storing pressures during analysis of a standard sample at certain time intervals from the sample injection, detecting and storing pressures during analysis of an unknown sample under the same conditions in a like manner, and comparing the pressure value data in the same instant after the sample injection to each other, it is possible to confirm whether the apparatus components, such as feeding devices including the pump 5, the valves 3, 4 for changing the composition of the eluent, and the column thermostat 8*a*, have operated normally or not, i.e., whether those apparatus components have operated in the same manner as during analysis of the standard sample.

FIG. 8 is a representation of one example of an analysis result report obtained by the apparatus for chromatographic analysis of this embodiment. The name of pressure data file created by detecting and storing the pressures at time intervals of 10 seconds from the sample injection is output along with the analysis date, the output date, the name of the analytical process file, and the name of the data file. The pressure transition agreement output subsequent to concentrations of respective components is given by comparing the pressure file (whose name is PAH001, PRS in FIG. 8), which is to be compared as a reference and created by detecting and storing pressures at time intervals of 10 seconds from the sample injection during analysis of a standard sample, and the pressure values (pressure data file: PAH005, PRS in FIG. 8) obtained from the current analysis (of an unknown sample). In the case of FIG. 8, ratios of two data values in the instant time after the sample injection are calculated and one of the calculated ratio values which is most away from 1 among all the data is output as the pressure transition agreement.

FIG. 9 is a representation of another example of analysis result reports obtained from the apparatus for chromatographic analysis of this embodiment. The pressure transition agreement is calculated and output in the same manner as in FIG. 8. In FIG. 9, however, the pressure values obtained from the current analysis (of an unknown sample) is stored in a pressure data file: PAH006, PRS. In this case, because the pressure transition agreement (ratio value) is 0.5 that is not within the range of 0.9 to 1.1 (see FIG. 4) preset as threshold values, an alarm message "pressure transition is abnormal" is output additionally.

While the embodiment shown in FIGS. 4, 8 and 9 has been described as calculating ratios of two data values in the instant time after the sample injection, outputting as the pressure transition agreement one of the calculated ratio values which is most away from 1, and comparing the output ratio value with the preset threshold values to determine whether the agreement is within the range of the threshold values, it is also possible to calculate differences between two data values in the instant time after the sample injection, output as the pressure transition agreement one of the calculated difference values which is most away from 0, and compare the output ratio value with the preset threshold values to determine whether the agreement is within the range of the threshold values.

In other words, whether the apparatus is operating normally or not can be easily and objectively judged by, when an unknown sample is measured, selecting a file of the pressure transition data obtained from a standard sample or an objective sample analyzed in the past which is to be compared as a reference, calculating a ratio or a difference between the detected pressure values of the unknown sample and the values of the selected pressure transition data in the same instant from the sample injection, and determining an agreement between both the values. Further, since the pressure transition data which has resulted from detecting an unknown sample is compared with the pressure transition data which has resulted from analyzing a standard sample or an objective sample in the past under the same conditions, the embodiment can also be applied to the case where analysis is performed while changing the composition and/or feeding conditions of the eluent.

According to the present invention, as described above, when an unknown sample is measured, the pressure transition data which is to be compared as a reference is selected from data files previously stored, the detected pressure values of the unknown sample are compared in a comparator with the values of the selected pressure transition data, and an agreement between both the values is determined. It is therefore possible to easily and objectively judge whether the apparatus is operating normally or not. Further, since the pressure transition data which has resulted from detecting an unknown sample is compared with the pressure transition data which has resulted from analyzing a standard sample or an objective sample in the past under the same conditions, the present invention is also adaptable for the case where analysis is performed while changing the composition and/or feeding conditions of the eluent.

What is claimed is:

1. An apparatus for chromatographic analysis which includes the steps of feeding an eluent by a pump, injecting a sample into said eluent from a sample injector, passing a mixture of said eluent and said sample through a column, and performing identification and quantitative measurement of said sample by a data processor based on component peaks occurred in said column, wherein said apparatus comprises a pressure sensor for detecting the pressure of said eluent in a feed path, a pressure memory for storing the pressure values detected at certain time intervals from the start of measurement as a data file of pressure transition data for each sample, a selector for, when an unknown sample is measured, selecting the pressure transition data, which is to be compared as a reference, from data files stored beforehand, and a comparator for comparing the pressure values of the unknown sample detected by said pressure sensor and the values of said pressure transition data selected by said selector and determining the results of the comparison of both the values.

2. An apparatus for chromatographic analysis according to claim 1, wherein said comparator calculates, as a numerical value, the results of the comparison between said detected pressure values of the unknown sample and the values of said pressure transition data selected from said data files in the same instant after the start of measurement.

3. An apparatus for chromatographic analysis according to claim 2, wherein said comparator takes differences between said detected pressure values of the unknown sample and the values of said pressure transition data selected from said data files.

4. An apparatus for chromatographic analysis according to claim 2, wherein said comparator takes ratios between said detected pressure values of the unknown sample and the values of said pressure transition data selected from said data files.

5. An apparatus for chromatographic analysis according to claim 2, further comprising an output unit for outputting the results of the comparison of said values calculated as a numerical value by said comparator along with the results of said identification and said quantitative measurement of the sample.

6. An apparatus for chromatographic analysis according to claim 5, further comprising a threshold value setting unit for presetting threshold values for said results of the comparison of said values calculated as a numerical value, wherein said comparator compares said results calculated as a numerical value and said threshold values, and said output unit outputs an alarm message when said results calculated as a numerical value are not within the range of said threshold values.

7. An apparatus for chromatographic analysis comprising a pump for feeding an eluent, an injector for injecting a sample into said eluent, a column allowing a mixture of said sample and said eluent to pass therethrough for separation of said sample into components, and a detector for performing identification of said sample based on the separation of said sample into components in said column, wherein said apparatus further comprises a pressure sensor for detecting the pressure of said eluent in a feed path, estimates a pressure depending on the composition of said eluent, and compares the pressure detected by said pressure sensor with said estimated pressure.

8. An apparatus for chromatographic analysis comprising a pump for feeding an eluent, an eluent supply unit for changing the composition of said eluent over time, an injector for injecting a sample into said eluent, a column allowing a mixture of said sample and said eluent to pass therethrough for separation of said sample into components, and a detector for performing identification of said sample based on the separation of said sample into components in said column, wherein said apparatus further comprises a pressure sensor for detecting the pressure of said eluent in a feed path, obtains a pressure depending on change in the composition of said eluent, and compares the pressure detected by said pressure sensor with said obtained pressure.

9. An apparatus for chromatographic analysis comprising a pump for feeding an eluent, an injector for injecting a sample into said eluent, a column allowing a mixture of said sample and said eluent to pass therethrough for separation of said sample into components, and a detector for performing identification of said sample based on the separation of said sample into components in said column, wherein said apparatus further comprises a pressure sensor for detecting the pressure of said eluent in a feed path, stores a plurality of measured values during a period from the start to the end of analysis performed in the past, obtains a pressure of said eluent from said stored values, and compares the pressure detected by said pressure sensor with said obtained pressure.

10. A method for chromatographic analysis comprising the steps of feeding an eluent by a pump, injecting a sample into said eluent from an injector, changing the composition of said eluent over time, passing a mixture of said sample and said eluent through a column, and performing identification of said sample based on separation of said sample into components in said column, wherein a pressure of said eluent in a feed path is detected, a pressure depending on the composition of said eluent is estimated and said detected pressure is compared with said estimated pressure.

* * * * *